US008604234B2

(12) United States Patent
Paul et al.

(10) Patent No.: US 8,604,234 B2
(45) Date of Patent: Dec. 10, 2013

(54) METHOD FOR PREPARING ACROLEIN FROM GLYCEROL BY CATALYTIC DEHYDRATION OF GLYCEROL USING A HETEROPOLYACID CATALYST

(75) Inventors: Sebastien Paul, Thun Saint-Amand (FR); Benjamin Katryniok, Loos-en-Gohelle (FR); Franck Dumeignil, Fretin (FR); Mickael Capron, Hasnon (FR)

(73) Assignees: Adisseo France S.A.S. (FR); Centre National de la Recherche Scientifique (FR); Universite Lille 1-Sciences et Technologies (FR)

( * ) Notice: Subject to any disclaimer, the term of this patent is extended or adjusted under 35 U.S.C. 154(b) by 0 days.

(21) Appl. No.: 13/516,113

(22) PCT Filed: Dec. 21, 2010

(86) PCT No.: PCT/FR2010/052855
§ 371 (c)(1),
(2), (4) Date: Aug. 15, 2012

(87) PCT Pub. No.: WO2011/083254
PCT Pub. Date: Jul. 14, 2011

(65) Prior Publication Data
US 2012/0330049 A1     Dec. 27, 2012

(30) Foreign Application Priority Data
Dec. 21, 2009   (FR) ..................................... 09 59276

(51) Int. Cl.
*C07C 45/29*     (2006.01)
*C07C 253/00*    (2006.01)
*C07C 51/235*    (2006.01)
*C07C 319/00*    (2006.01)

(52) U.S. Cl.
USPC ........... 558/315; 558/316; 560/147; 562/869; 568/42; 568/43; 568/486; 568/492

(58) Field of Classification Search
USPC ............ 558/311–316; 586/486; 562/531, 532
See application file for complete search history.

(56) References Cited

U.S. PATENT DOCUMENTS 7,790,934 B2 *  9/2010  Redlingshofer et al. ...... 568/486

FOREIGN PATENT DOCUMENTS

| WO | 2007/058221 A1 | 5/2007 |
| WO | 2008006977 A1 | 1/2008 |
| WO | 2009/127889 A1 | 10/2009 |

OTHER PUBLICATIONS

Tsukuda, E.; et al. Catal. Commun. 2007, 8, 1349-1353.*
Dongyuan Zhao et al. "Triblock Copolymer Syntheses of Mesoporous Silica with Periodic 50 to 300 Angstrom Pores", Science, 1998, pp. 548-552, vol. 279, downloaded from www.sciencemag.org; May 17, 2012, DOI: 10.1126/science.279.5350.548.
Erik Tsukuda, et al. "Production of acrolein from glycerol over silica-supported heteropoly acids", Catalysis Communications, 2007, pp. 1349-1353, vol. 8, Elsevier B.V.
Freddy Kleitz, et al. "Cubic 1a3d large mesoporous silica: synthesis and replication to platinum nanowires, carbon nanorods and carbon nanotubes", The Royal Society of Chemistry, ChemComm, 2003, pp. 2136-2137, Cambridge UK.
H. Atia, et al. "Dehydration of glycerol in gas phase using heteropolyacid catalysts as active compounds", Journal of Catalysis, Academic, Aug. 15, 2008, pp. 71-82, vol. 258, No. 1, Academic Press, Duluth, MN USA.
Lili Ning, et al. "Glycerol Dehydration to Acrolein over Activated Carbon-Supported Silicotungstic Acids", Chinese Journal of Catalysis, Mar. 2008, pp. 212-214, vol. 29, No. 3.
Mario Pagliaro, et al. "The Future of Glycerol: New Uses of a Versatile Raw Material: Dehydration", RSC Green Chemistry Book Series, 2008, pp. 54-64, Chapter 5.
Mario Pagliaro, et al. "From Glycerol to Value-Added Products", Angewandte Chemie Int. Ed., 2007, pp. 4434-4440, vol. 46, DOI: 10.1002/anie.200604694.
N.G. Kostova, et al. "Hexagonal mesoporous silicas with and without Zr as supports for HDS catalysts", Catalysis Today, 2001, pp. 217-223, vol. 65.
Oliver Y. Gutierrez, et al. "Mo and NiMo catalysts supported on SBA-15 modified by grafted ZrO2 species: Synthesis, characterized and evaluation in 4,6-dimethyldibenzothiophene hydrodesulfurization", Journal of Catalysis, 2007, pp. 140-153, vol. 249, Elsevier Inc.
Song-Hai Chai, et al. "Sustainable production of acrolein: Preparation and characterization of zirconia-supported 12-tungstophosphoric acid catalyst for gas-phase dehydration of glycerol", Applied Catalysis A: General, 2009, pp. 213-222, vol. 353, Elsevier B.V.
Written Opinion for International Patent Application No. PCT/FR2010/052855, International Application Filing Date Dec. 21, 2010; Date of Mailing Jan. 8, 2012, 6 pages.

* cited by examiner

*Primary Examiner* — Samantha Shterengarts
*Assistant Examiner* — Amanda L Aguirre
(74) *Attorney, Agent, or Firm* — Cantor Colburn LLP

(57) ABSTRACT

The invention relates to a method for preparing acrolein from glycerol or glycerin, according to which dehydration of glycerol or glycerin is carried out in the presence of a catalyst which consists in at least one silica modified with zirconium dioxide, titanium dioxide or tungsten trioxide or any combination of these oxides, and a heteropolyacid. This method may be used for making 3-(methylthio)propionic aldehyde (MMP), 2-hydroxy-4-methylthiobutyronitrile (HMBTN), methionine or its analogs, from acrolein.

22 Claims, 1 Drawing Sheet

METHOD FOR PREPARING ACROLEIN FROM GLYCEROL BY CATALYTIC DEHYDRATION OF GLYCEROL USING A HETEROPOLYACID CATALYST

TECHNICAL FIELD

The present invention relates to a catalytic method for making acrolein by dehydration of glycerol or glycerin and to the applications of such a method.

BRIEF DISCUSSION OF RELATED ART

By glycerol is meant a glycerol either purified or not, preferably stemming from biomass, and notably a highly purified or partly purified glycerol. A purified glycerol has a purity of more than or equal to 98%, obtained by distillation of glycerin. By glycerin is notably meant glycerin of natural origin, stemming from the hydrolysis of vegetable oils and animal fats, or a glycerin of synthetic origin, stemming from petroleum, more or less purified or refined, or else crude. Thus, in the following description, reference will mainly be made to the conversion of glycerol or glycerin stemming from biomass, but the invention is of course not limited thereto and its benefit extends to all glycerol and glycerin regardless of their origin and degree of purity.

Gradual depletion of fossil energies leads the industrialists to contemplate the use of renewable raw materials stemming from biomass for producing fuels. In this context, biodiesel is a fuel produced from vegetable or animal oil.

This product benefits from a green aura because of a clearly favorable $CO_2$ balance as compared with fossil energies. The DIESTER® (or VOME, vegetable oil methyl esters) is a biodiesel made by transesterification of triglycerides present in oleaginous liquids, notably vegetable oils of coprah, rapeseed and sunflower, by methanol, and (depending on the contemplated methods) coproduces approximately 100 kg of glycerol per ton of DIESTER®. The non-lipid portion of the raw material used, cakes, is mainly put to use in animal feed.

This biodiesel is used as a mixture in gas oil. European directives 2001/77/EC and 2003/30/EC, which will be applied in the near future, project the introduction of 7% in 2010 and 10% by the year of 2015 of DIESTER® in gas oil. This substantial increase in the amount of produced biodiesel will generate significant amounts of glycerol equivalent to several hundred thousand tons/year.

About 1,500 uses of glycerol have already been listed, among which the following illustrate as examples its presence in numerous and various formulations:

- moisturizers in pharmacy (in suppositories and syrups) or in cosmetology in moisturizing creams, glycerin soaps, tooth paste,
- solvents in the food industry,
- plasticizers or lubricants in the chemical industry.

These applications will prove to be clearly insufficient for absorbing the amounts of glycerol which will be produced with biodiesels and although they are in progress, the conventional glycerol market (soaps, pharmacy, . . . ) will not either be able to absorb such a surplus. It is therefore vital to find new applications with which very large volumes of glycerol may be put to full use.

In front of this statement of fact, many outlets have been investigated these recent years (see M. Pagliaro et al., *Angew. Chem. Int. Ed.* (2007) 46, 4434-4440 as well as M. Pagliaro, M. Rossi: The Future of Glycerol, RSC Publishing, Cambridge (2008)), with, in particular, six following beneficiation routes:

- conversion into 1,3-propanediol and into 1,2-propanediol, notably used as base monomers in the synthesis of polyesters and polyurethanes,
- conversion into monoesters for chemistry of lubricants,
- conversion into polyglycerols which are used as emulsifiers, food additives,
- conversion into acrolein (by dehydration) and into acrylic acid (by dehydration and oxidation),
- direct beneficiation as additives for animal feed.

Acrolein and acrylic acid are traditionally produced by controlled oxidation in the gas phase of propylene by oxygen from air in the presence of catalysts based on molybdenum and/or bismuth oxides. The thereby obtained acrolein may either be directly integrated into a two-step method for making acrylic acid, or be used as a synthesis intermediate. The production of these two monomers is therefore closely related to propylene which as a substance is made by vapocracking or catalytic cracking of petroleum cuts.

The markets of acrolein, the simplest of unsaturated aldehydes, and of acrylic acid are gigantic since these monomers enter the composition of many mass products.

Moreover, acrolein, a highly reactive compound because of its structure, finds many applications, notably as a synthesis intermediate, it is most particularly used as a key intermediate entering the synthesis of D,L-methionine and of its hydroxy-analog derivative, 2-hydroxy-4-methylthiobutanoic acid (HMTBA). These food additives are massively used since they enter the composition of food supplements indispensable for the growth of animals (poultry, pigs, ruminants, fish, . . . ). In a certain number of cases, it may be beneficial to be able to increase, or even ensure production capacities of existing industrial units by diversifying the engaged raw material. Most particularly it therefore appears to be of interest to be able to increase the productivity of acrolein, while reducing dependency with regard to this fossil resource which propylene is.

BRIEF SUMMARY

The invention lies in the application of robust, active, selective and regenerable catalysts, with which acrolein may be directly produced from glycerol or glycerin, notably from biomass, according to the reaction:

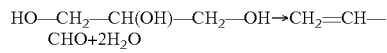

$$HO-CH_2-CH(OH)-CH_2-OH \rightarrow CH_2=CH-CHO+2H_2O$$

With this alternative it is thereby possible to have a competitive synthesis method of acrolein which does not depend on the propylene petroleum resource, from another renewable raw material.

This possibility is particularly advantageous for the synthesis of methionine or its analogs, such as its hydroxy-analog (HMTBA), directly from the biomass.

Thus, the invention further relates to an application of this reaction to the synthesis of 3-(methylthio)propionic aldehyde (MMP), 2-hydroxy-4-methylthiobutyronitrile (HMTBN), methionine and of its analogs such as 2-hydroxy-4-methylthiobutanoic acid (HMTBA), HMTBA esters such as isopropyl ester, and 2-oxo-4-methylthiobutanoic acid, from acrolein.

Methionine, HMTBA and analogs of the latter, are used in animal nutrition, and in their industrial synthesis methods, acrolein is generally obtained by oxidation of propylene and/or propane. Oxidation of propylene into acrolein by air in the presence of water is partial, and the resulting crude product based on acrolein also contains unreacted propylene and propane, water and byproducts of the oxidation reaction, notably acids, aldehydes and alcohols.

It has been known for a long time that glycerol (also called glycerin) decomposes giving off acrolein when it is brought to temperatures above 280° C. This slightly selective reaction is accompanied by the formation of many byproducts including acetaldehyde, hydroxyacetone, in addition to total oxidation products CO and $CO_2$. It is therefore indispensable to control, by the action of a catalyst, the reaction for transforming glycerol into acrolein in order to do without any subsequent costly separation in terms of energy and any complex method for purifying acrolein.

Many academic and industrial researchers have investigated this reaction. Use of supercritical water as a reaction medium was notably envisioned, which allows it to be placed in an acid medium by acting on the temperature and pressure of the reaction medium and therefore save on the use of a catalyst. However, the use of a supercritical solvent at an industrial scale remains difficult for a continuous method because of the particularly heavy infrastructure which it requires (autoclave operating under very high pressure and withstanding a particularly corrosive medium).

On the other hand, the setting up of a continuous method in a gas phase and at atmospheric pressure becomes conceivable if a performing, selective and resistant catalytic system is identified and applied. In front of the increasing advantage of such an alternative, the literature mentions a large number of studies relating to the use of catalytic systems based on supported phospho- or silico-tungstic heteropolyacids, mixed oxides and zeolites, which may be used for continuous or discontinuous methods in a liquid phase or in a gas phase.

Thus, Tsukuda et al. (Cat. Comm. (2007), 8, 1349), Chai et al., (Appl. Catal. A (2009) 353, 213) and Ning et al., (J. Catal. (2008), 29, 212) describe methods for catalytic dehydration of glycerol into acrolein in the gas phase, which apply strongly acid catalysts in the form of a heteropolyacid supported on silica, on active coal or on zirconium oxide. Dubois et al. (WO 2009/127889) propose a method for dehydrating glycerol by using as catalyst alkaline salts of heteropolyanionic acids. It is noted in these investigations that the formation of coke at the surface of the catalysts very rapidly poisons the latter and that it is thereby often necessary to regenerate the catalyst in order to again find satisfactory catalytic activity.

As compared with known methods, the present invention provides a method for preparing acrolein from glycerol or crude glycerol, by catalytic dehydration of glycerol in the presence of a catalyst which, while allowing conversion of the totality of the initial glycerol, at the same time may be very easily regenerated and has excellent acrolein selectivity as well as a long lifetime.

The authors of the invention have discovered that this catalyst consisted in at least one inorganic acid and silica modified by zirconium dioxide, titanium dioxide, or tungsten trioxide or any combination of these oxides.

The inorganic acid according to the invention is selected from heteropolyacids (HPA) and preferably from phospho-tungstic acid, silicotungstic acid and phosphomolybdic acid, and their heterosubstitutes. Preferably, the HPAs of the invention are based on tungsten.

The heteropolyacids (HPA) are oxygenometallic atomic structures well-known to one skilled in the art, generally formed by a core of atoms of a single element or of different elements, for example selected from those of Groups I-VIII of the Periodic Table of Elements, silicon and phosphorus being preferred, around which are symmetrically distributed peripheral atoms of a single element or of different elements, often selected from molybdenum, tungsten, vanadium, niobium, tantalum and other metals. The HPAs are the acid form of heteropolyanions, notably those of the Keggin type and those of the Dawson type. In the HPA designation according to the invention, said heteropolyanions are included. By heterosubstitutes of an HPA are meant according to the invention, HPAs in the structure of which one or more atoms have been substituted with other atoms, thus, $H_4PMo_{11}VO_{40}$ is a heterosubstitute of the HPA $H_3PMo_{12}VO_{40}$.

The silica of this invention is selected from amorphous silicas or more favorably from mesoporous silicas such as commercially available SBA-15, SBA-16, MCM-41 or KIT-6 and then modified by zirconia.

According to an alternative of the invention, the heteropolyacid is supported on modified silica.

Thus, the catalyst is obtained by modification of the silica with the zirconium dioxide followed by calcination at high temperature and then by impregnation of the support with the inorganic acid.

The support may be prepared in various ways, such as impregnation, grafting, co-precipitation, hydrothermal synthesis, which are techniques well-known to one skilled in the art. A procedure for preparing mesoporous silica was described by Kleitz et al. (Chem. Com. (2003) 17 2136), Zhao et al. (Science (1998) 279, 548). A procedure for modifying silica with zirconium dioxide was described by Gutierrez et al. (J. Catal. (2007), 249, 140) as well as by Kostova et al. (Catal. Today (2001), 65, 217).

The catalyst defined earlier may further fit the preferential characteristics below, considered alone or as a combination:

the zirconium dioxide/silica mass ratio varies from 0.02 to 5, more advantageously it varies from 0.05 to 1, the Ti dioxide/silica mass ratio varies from 0.02 to 5, more advantageously it varies from 0.05 to 1, the W trioxide/silica mass ratio varies from 0.02 to 5, more advantageously it varies from 0.05 to 1, the Zr dioxide/Ti dioxide/silica mass ratio varies from 0.02/0.02/1 to 2/2/1, more advantageously it varies from 0.05/0.05/1 to 1/1/1, the Zr dioxide/W trioxide/silica mass ratio varies from 0.02/0.02/1 to 2/2/1, more advantageously it varies from 0.05/0.05/1 to 1/1/1, the Ti dioxide/W trioxide/silica mass ratio varies from 0.02/0.02/1 to 2/2/1, more advantageously it varies from 0.05/0.05/1 to 1/1/1, the Zr dioxide/Ti dioxide/W trioxide/silica mass ratio varies from 0.02/0.02/0.02/1 to 2/2/2/1, more advantageously it varies from 0.05/0.05/0.05/1 to 1/1/1/1, the calcination temperature of the support varies from 50 to 1,200° C., more advantageously from 450 to 750° C., the inorganic acid/support mass ratio varies from 0.02 to 5, more advantageously it varies from 0.05 to 1.

As stated earlier, and as illustrated by the examples hereafter, the catalyst of the invention has the advantage of being able to be easily regenerated, and this without affecting the yield of the dehydration, or the acrolein selectivity. Thus, in the invention provides the method described above in which the catalyst is regenerated.

When the reaction for converting glycerol into acrolein is conducted in a gas phase, different method technologies may be used, i.e. in a fixed bed, in a fluidized bed or in a flowing fluidized bed. In the first two methods, the regeneration of the catalyst may be separate from the reaction. For example, it may be accomplished ex situ with conventional regeneration methods, such as combustion in air or with a gas mixture containing molecular oxygen. According to the method of the invention, regeneration may also be accomplished in situ since the temperatures and pressures at which regeneration is accomplished are close to the reaction conditions of the method.

Another advantage of the method of the invention lies in the form of the initial glycerol or glycerin, which may be in a pure or partly purified form or in solution, notably in an aqueous solution. Advantageously, an aqueous solution of glycerol is used. In an aqueous solution, the concentration of glycerol is preferably of at least 1% by mass, at best it varies from 5 to 50% by mass and preferably is between 10 and 30% by mass. Advantageously, the glycerol concentration should not be too high in order to avoid parasitic reactions which burden the yield in acrolein, such as formation of glycerol ethers or acetalization reactions between the produced acrolein and the unconverted glycerol. Moreover, the solution of glycerol should not be too diluted, because of the redhibitory energy cost introduced by evaporation of water. In every case, it is easy to adjust the concentration of the glycerol solution by partly or totally recycling the water produced by the relevant reaction.

The invention further provides a method for making 3-(methylthio)propionic aldehyde (MMP), 2-hydroxy-4-methylthiobutyronitrile (HMBTN), methionine or its aforementioned analogs from acrolein, according to which acrolein is obtained by a method as described above. Comparatively to the conventional method for making acrolein by controlled oxidation of propylene, the acrolein produced according to the aforementioned method may contain impurities different from those of the traditional method, both under the angle of their amounts and of their nature. According to the envisioned use, synthesis of acrylic acid or of methionine or of its analogs, purification of acrolein according to techniques known to one skilled in the art may be considered, for example the one described in document WO2008/006977A in the name of the Applicant.

Thus, once the acrolein is directly obtained according to the invention or after purification, it is reacted with methylmercaptan (MSH) in order to produce 3-(methylthio)propionic aldehyde (or MMP). In a following step, the MMP is put into contact with hydrocyanic acid in order to produce 2-hydroxy-4-(methylthio)butyronitrile (HMBTN). After synthesis of HMBTN, various reaction steps lead to methionine and its analogs including the hydroxy-analog (HMTBA). All these steps from the synthesis of acrolein are well known to one skilled in the art.

DETAILED DESCRIPTION

The present invention will now be described in more detail and illustrated with examples and figures hereafter without however limiting the scope thereof.

The reaction conditions and the calculation methods used for determining the conversion and the acrolein selectivity are described hereafter.

The dehydration reaction of glycerol is conducted on the catalyst, at atmospheric pressure, in a tubular reactor with a fixed bed of a diameter of 15 mm and of a length of 120 mm. The reactor is placed in an oven which allows the catalyst to be maintained at the reaction temperature, typically 275° C. The mass of catalyst loaded in the reactor is 0.3 g (about 1 mL). The reactor is supplied with a flow rate of 1.5 g/h of aqueous solution with 10% by mass of glycerol. The aqueous solution of glycerol is vaporized on an inert solid in the presence of a flow of helium of 30 mL/min. The relative glycerol/water/nitrogen molar proportions are 1.1/50.7/48.1.

The calculated contact time is of the order of 0.7 s, i.e. a GHSV of 6,000 $h^{-1}$. The contact time and the GHSV are defined as follows:

GHSV=glycerol volume flow rate/catalyst volume

Contact time=catalyst volume/total volume flow rate

Total volume flow rate at 275° C.=volume flow rate of the glycerol+volume flow rate of the water+volume flow rate of the inert gas.

After the reaction, the products are condensed in a cooled trap by means of a cryostat bath. For better trapping, the traps contain an initial known mass of water. The trapping time is one hour and the supply flow is not interrupted during the trap changes carried out every hour.

The formed products are analyzed by gas chromatography as well as by high-performance liquid chromatography.

the main products of the reaction are analyzed by liquid chromatography (column THERMO HyperRez, 250 mm, 8 μm particles) with a chromatograph THERMO SpectraSystem provided with an RI detector (THERMO Surveyor plus). The quantified products during this analysis are: acrolein, acetol, allyl alcohol and glycerol.

The conversion of glycerol, the acrolein selectivity and the yields of the different products are defined as follows:

Conversion of glycerol 'C'(%)=100×(1−remaining glycerol molar flow rate/introduced glycerol molar flow rate);

Acrolein selectivity 'S'(%)=100×(produced acrolein molar flow rate/reacted glycerol molar flow rate);

Acrolein yield 'R'(%)=100×X product molar flow rate/introduced glycerol molar flow rate.

The invention is illustrated hereafter through the following examples which give details thereof and the advantages as compared with the prior art and supporting the figures according to which:

EXAMPLE 1

Figure 1:
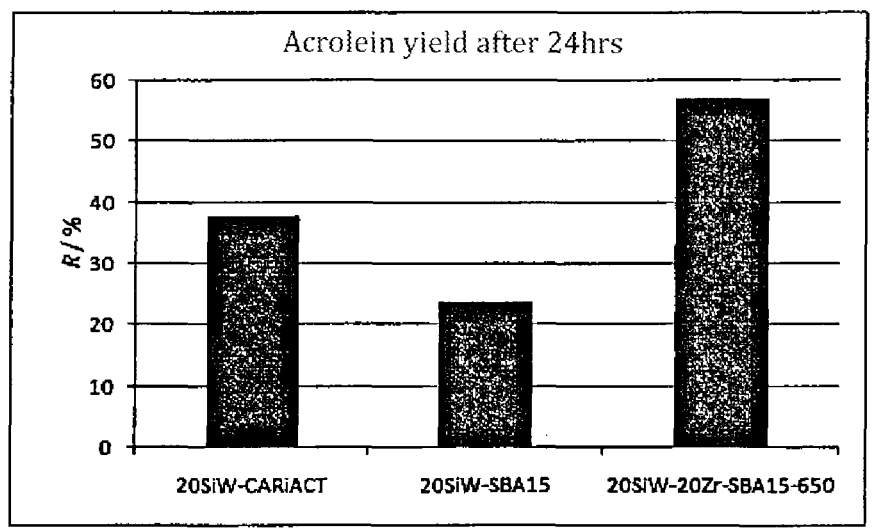
FIG. 1 illustrates a comparison of the acrolein yield after 24 hrs for 20SiW-CARiACT and 20SiW-SBA15 catalysts (Example 2) and 20SiW-20Zr-SBA15-650 (Example 1a).
Figure 2:
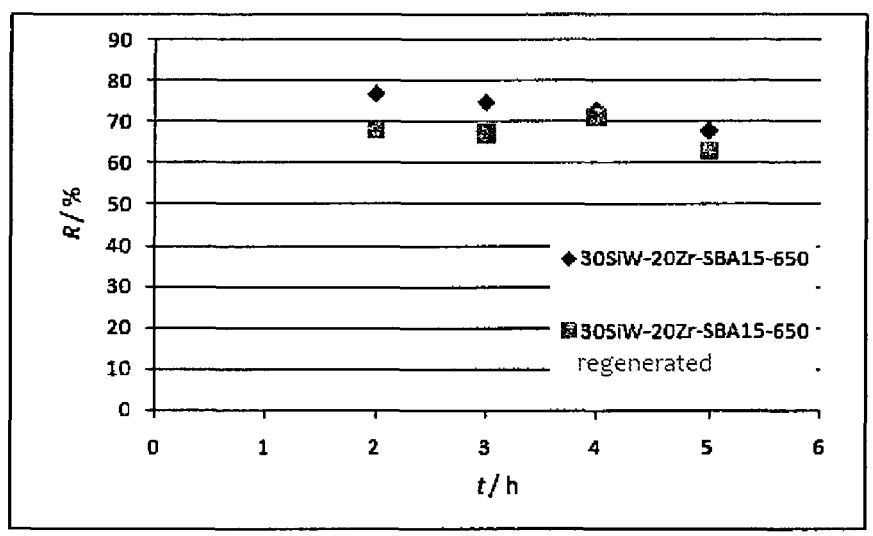
FIG. 2 illustrates a comparison of the acrolein yield over time, with the catalyst 30SiW-20Zr-SBA15-650 before regeneration (Example 1a) and after regeneration (Example 3). The indicated time for each point is that of the end of trapping with a duration of one hour.

Preparation and Characterization of Silica-Supported Catalysts Modified by Zirconia Grafting, According to the Invention Modification of Silica:

The example deals with different silicas which have a specific surface area varying from 250 $m^2$/g to 700 $m^2$/g, and the pore size of which varies from 5 nm to 12 nm.

1) The silica support of the SBA-15 type is either obtained commercially, or prepared according to the procedure described in the literature (see for example Zhao et al., Science (1998), 279, 548). A synthesis example thereof is given below:

3.2 g of polyethylene glycol (5,800 g/mol) are dissolved in a solution containing 101 mL of distilled water and 8.7 mL of hydrochloric acid (37%) at 45° C. 6.5 g of tetraethyl-ortho-silicate (99.9%) are then added. The solution is left with stirring for 24 hrs and then transferred into a Teflon autoclave. The autoclave containing the solution is then heated to 140° C. for 24 hrs. The silica SBA-15 is obtained by filtration. After drying at 100° C. the silica is calcinated in air at 550° C. for 3 hrs. This is a mesoporous silica of hexagonal structure.

2) The silica support of type KIT-6 is obtained either commercially or prepared according to a procedure described in the literature (see for example Kleitz et al., Chem. Com. (2003), 17, 2136). A synthesis example thereof is given below:

9 g of polyethylene glycol (5,800 g/mol) are dissolved in a solution containing 325 mL of distilled water and 18 mL of hydrochloric acid (32%) at 35° C. 9 g of n-butanol (99%) and 6.5 g of tetraethyl-ortho-silicate (99.9%) are then added. The solution is left with stirring for 24 hrs before being transferred into a Teflon autoclave. The autoclave containing the solution is heated to 100° C. for 24 hrs. The silica KIT-6 is obtained by filtration. After drying at 100° C., the silica is calcined in air at 550° C. for 3 hrs.

It is a mesoporous silica of cubic structure.

3) The silica support of type CARiACT-Q10 is obtained commercially from Fuji Silysia Chemical LTD (Japan). It is a mesoporous silica of hexagonal structure.

The silica supports are then modified by grafting with zirconium dioxide (zirconia) according to a method described in the literature by Gutierrez et al., J. Catal. (2007), 249, 140. The standard procedure for preparing a 20% zirconia support is the following:

To a gel of 0.8 g of silica and of 20 mL of ethanol (extra dry) are added 0.76 g of zirconium isopropylate (70%). The gel is then left with stirring until total evaporation of the liquid substrate. After drying at 100° C., the silica is calcined in air at 650° C. for 3 hrs.

The supports are then impregnated with silicotungstic acid. The procedure for preparing a catalyst with 20% by mass of acid is the following: 0.8 g of support is suspended in 20 mL of distilled water. A solution of 0.2 g of silicotungstic acid $H_4SiW_{12}O_{40}$ in 2 mL of distilled water is added to the suspension, and then the solvent is totally evaporated.

The catalysts are referenced subsequently in the text in the following way:

XSiW-YZr-Sup-T

With:

X=silicotungstic acid content (% by mass in the final catalyst);

Y=zirconium dioxide content (% by mass of the final support);

Sup=type of silica (KIT6=KIT-6, SBA15=SBA-15, CARiACT=CARiACT-Q10);

T=calcination temperature in ° C.

EXAMPLE 1a

Influence of the Heteropolyacid (HPA) Content

TABLE 1a

| Catalyst | 1-5 hrs | | | 24-25 hrs | | | 30-31 hrs | | |
|---|---|---|---|---|---|---|---|---|---|
| | C/% | S/% | R/% | C/% | S/% | R/% | C/% | S/% | R/% |
| 10SiW—20Zr-SBA15-650 | 87 | 49 | 42 | 70 | 44 | 31 | — | — | — |
| 20SiW—20Zr-SBA15-650 | 96 | 74 | 71 | 78 | 88 | 69 | 66 | 87 | 57 |
| 30SiW—20Zr-SBA15-650 | 89 | 75 | 67 | 66 | 78 | 52 | 62 | 77 | 48 |

EXAMPLE 1b

Influence of the Zirconium Dioxide Content

TABLE 1b

| Catalyst | 1-5 hrs | | | 24-25 hrs | | | 30-31 hrs | | |
|---|---|---|---|---|---|---|---|---|---|
| | C/% | S/% | R/% | C/% | S/% | R/% | C/% | S/% | R/% |
| 20SiW—0Zr-SBA15-650 | 84 | 83 | 70 | 41 | 57 | 24 | — | — | — |
| 20SiW—10Zr-SBA15-650 | 87 | 77 | 67 | 62 | 69 | 43 | 69 | 55 | 38 |
| 20SiW—20Zr-SBA15-650 | 96 | 74 | 71 | 78 | 88 | 69 | 66 | 87 | 57 |
| 20SiW—40Zr-SBA15-650 | 90 | 65 | 59 | 60 | 44 | 26 | 40 | 63 | 25 |

EXAMPLE 1c

Influence of the Support

TABLE 1c

| Catalyst | 1-5 hrs | | | 24-25 hrs | | |
|---|---|---|---|---|---|---|
| | C/% | S/% | R/% | C/% | S/% | R/% |
| 20SiW—20Zr-KIT6-650 | 95 | 66 | 62 | 75 | 45 | 34 |
| 20SiW—20Zr-SBA15-650 | 96 | 74 | 71 | 78 | 88 | 69 |
| 20SiW—20Zr-CARiACT-650 | 92 | 82 | 76 | 60 | 73 | 44 |

EXAMPLE 1d

Influence of the Calcination Temperature

TABLE 1d

| Catalyst | 1-5 hrs | | | 24-25 hrs | | | 30-31 hrs | | |
|---|---|---|---|---|---|---|---|---|---|
| | C/% | S/% | R/% | C/% | S/% | R/% | C/% | S/% | R/% |
| 20SiW—20Zr-SBA15-0 | 68 | 44 | 30 | 45 | 47 | 21 | — | — | — |
| 20SiW—20Zr-SBA15-400 | 92 | 61 | 56 | 67 | 51 | 34 | 54 | 56 | 30 |
| 20SiW—20Zr-SBA15-650 | 96 | 74 | 71 | 78 | 88 | 69 | 66 | 87 | 57 |
| 20SiW—20Zr-SBA15-950 | 91 | 77 | 70 | 46 | 62 | 29 | 35 | 61 | 22 |

EXAMPLE 2

Preparation and Characterization of the Catalyst of the Non Modified Silica Type (Comparative Example of the Prior Art)

These catalysts of the prior art consist of HPA supported on a non-modified silica. The nature of the HPAs and the non-modified silicas are the same as those of Example 1.

The catalysts of the comparative example are based on silica of the CARiACT Q10 (Fuji Silysia Chemical LTD), SBA-15 and KIT-6 type impregnated with 20% by mass of silicotungstic acid $H_4SiW_{12}O_{40}$(SiW). The catalysts are referenced in the following way:

XSiW-Sup

With:

X=silicotungstic acid content (% by mass in the final catalyst);

Sup=type of silica (KIT6=KIT-6, SBA15=SBA-15, CARiACT=CARiACT-Q10);

TABLE 2

| Catalyst | 1-5 hrs | | | 24-25 hrs | | |
|---|---|---|---|---|---|---|
| | C/% | S/% | R/% | C/% | S/% | R/% |
| 20SiW-CARiACT | 97 | 80 | 78 | 58 | 66 | 38 |
| 20SiW-SBA15 | 84 | 83 | 70 | 41 | 57 | 24 |
| 20SiW-KIT6 | 97 | 78 | 76 | 68 | 66 | 45 |

Moreover, it is known from WO2007/058221, that silicotungstic acid supported on silica, Q10-SiW30 (30% of silicotungstic acid), which is also the subject of Tsukuda et al. (2007) above, exhibits the same catalytic performances that silicotungstic acid supported on silica (20% of silicotungstic acid).

EXAMPLE 3

Regeneration of the Catalyst

After 97 hours under the reaction mixture, the catalyst 30SiW-20Zr-SBA15-650 according to the invention is regenerated under an air flow at 275° C. for 2 hrs (air flow rate: 25 mL/min). After regeneration, the catalyst is tested under the same operating conditions as before the regeneration.

The obtained results are shown in the following table 3:

| Catalyst | 1-5 hrs | | |
|---|---|---|---|
| | C/% | S/% | R/% |
| 30SiW—20Zr-SBA15-650 fresh | 89 | 75 | 67 |
| 30SiW—20Zr-SBA15-650 After regeneration | 95 | 72 | 69 |

By regeneration with air at 275° C., the catalyst 30SiW-20Zr-SBA15-650 was able to recover its initial yield. The catalyst 30SiW-20Zr-SBA15-650 according to the invention may therefore be regenerated over a short time and without loss of activity or of selectivity. Not only, the catalyst 30SiW-20Zr-SBA15-650 is active and selective but it may also be entirely and easily regenerated.

The invention claimed is:

1. A method of preparing acrolein from glycerol comprising dehydration of glycerol carried out in the presence of a catalyst comprising at least one heteropolyacid and one silica, said silica being modified by grafting with zirconium dioxide, titanium dioxide or tungsten trioxide or any combination of these oxides, and said heteropolyacid being supported on a support comprising said modified silica.

2. The method according to claim 1, wherein said silica is modified by grafting with zirconium dioxide.

3. The method according to claim 1, wherein said silica is modified by grafting with titanium dioxide.

4. The method according to claim 1, wherein said silica is modified by grafting with tungsten trioxide.

5. The method according to claim 1, wherein the Zr dioxide/silica mass ratio varies from 0.02 to 5.

6. The method according to claim 1, wherein the Ti dioxide/silica mass ratio varies from 0.02 to 5.

7. The method according to claim 1, wherein the W trioxide/silica mass ratio varies from 0.02 to 5.

8. The method according to claim 1, wherein the Zr dioxide/Ti dioxide/silica mass ratio varies from 0.02/0.02/1 to 2/2/1.

9. The method according to claim 1, wherein the Zr dioxide/W trioxide/silica mass ratio varies from 0.02/0.02/1 to 2/2/1.

10. The method according to claim 1, wherein the Ti dioxide/W trioxide/silica mass ratio varies from 0.02/0.02/1 to 2/2/1.

11. The method according to claim 1, wherein the Zr dioxide/Ti dioxide/W trioxide/silica mass ratio varies from 0.02/0.02/0.02/1 to 2/2/2/1.

12. The method according to claim 11, wherein the heteropolyacid/support mass ratio varies from 0.02 to 5.

13. The method according to claim 1, wherein the heteropolyacid is based on tungsten.

14. The method according to claim 1, wherein the glycerol is in an aqueous solution, in a concentration of at least 1% by weight.

15. The method according to claim 14, wherein the concentration of the aqueous glycerol solution varies from 5 to 50% by weight.

16. The method according to claim 1, wherein the catalyst is regenerated.

17. The method according to claim 1, wherein the dehydration reaction is conducted in the gas phase.

18. The method according to claim 17, wherein the dehydration reaction is conducted in a reactor with a fixed bed, a fluidized bed or a circulating fluidized bed.

19. A method for making 3-(methylthio)propionic aldehyde (MMP), 2-hydroxy-4-methylthiobutyronitrile (HMBTN), methionine, 2-hydroxy-4-methylthiobutanoic acid (HMTBA), HMTBA esters, and 2-oxo-4-methylthiobutyronitrile, from acrolein, comprising the step of
preparing acrolein from glycerol according to the method of claim 1.

20. A method of preparing acrolein from glycerol comprising dehydration of glycerol in the presence of a catalyst,
wherein the catalyst consists of at least one heteropolyacid supported on a silica support modified by grafting with zirconium dioxide, and
wherein the heteropolyacid is selected from the group consisting of phosphotungstic acid, silicotungstic acid, phosphomolybdic acid, and their hetero-substitutes.

21. The method according to claim 20, wherein the glycerol is an aqueous glycerol solution comprising 5 to 50% by weight of glycerol.

22. The method according to claim 21, wherein the heteropolyacid is a silicotungstic acid.

* * * * *